US008247526B2

(12) United States Patent
Minter et al.

(10) Patent No.: US 8,247,526 B2
(45) Date of Patent: *Aug. 21, 2012

(54) PROCESS FOR THE PREPARATION OF POLYALKYLENE ETHER GLYCOL

(75) Inventors: Aaron Minter, Wilmington, DE (US); Edward R. Murphy, Lakeland, TN (US); James M. Tocyloski, North East, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/972,903

(22) Filed: Dec. 20, 2010

(65) Prior Publication Data

US 2012/0157657 A1 Jun. 21, 2012

(51) Int. Cl.
*C08G 65/34* (2006.01)

(52) U.S. Cl. ........ 528/425; 528/256; 528/679; 528/620; 568/623; 568/620; 568/679; 564/505

(58) Field of Classification Search .................. 528/425, 528/256, 679, 620; 568/623, 620, 679; 564/505
See application file for complete search history.

(56) References Cited

U.S. PATENT DOCUMENTS

| | | | |
|---|---|---|---|
| 2,520,733 A | 8/1950 | Morris et al. |
| 3,326,985 A | 6/1967 | Mason |
| 4,924,007 A | 5/1990 | Massonneau et al. |
| 5,015,789 A | 5/1991 | Arntz et al. |
| 5,089,583 A | 2/1992 | Nichols et al. |
| 5,149,844 A | 9/1992 | Nichols et al. |
| 5,274,123 A | 12/1993 | Deruelle et al. |
| 5,276,201 A | 1/1994 | Haas et al. |
| 5,284,979 A | 2/1994 | Haas et al. |
| 5,329,015 A | 7/1994 | Burk |
| 5,334,778 A | 8/1994 | Haas et al. |
| 5,364,984 A | 11/1994 | Arntz et al. |
| 5,364,987 A | 11/1994 | Haas et al. |
| 5,386,061 A | 1/1995 | Burk |
| 5,532,395 A | 7/1996 | Burk |
| 5,559,267 A | 9/1996 | Burk |
| 5,565,593 A | 10/1996 | Burk |
| 5,596,114 A | 1/1997 | Burk |
| 5,633,362 A | 5/1997 | Nagarajan et al. |
| 5,686,276 A | 11/1997 | Laffend et al. |
| 5,821,092 A | 10/1998 | Nagarajan et al. |
| 5,962,745 A | 10/1999 | Brossmer et al. |
| 6,140,543 A | 10/2000 | Brossmer et al. |
| 6,180,799 B1 | 1/2001 | Suri et al. |
| 6,232,511 B1 | 5/2001 | Haas et al. |
| 6,235,948 B1 | 5/2001 | Sunkara et al. |
| 6,277,289 B1 | 8/2001 | Kurian et al. |
| 6,297,408 B1 | 10/2001 | Haas et al. |
| 6,331,264 B1 | 12/2001 | Kurian et al. |
| 6,342,646 B1 | 1/2002 | Haas et al. |
| 6,428,767 B1 | 8/2002 | Burch et al. |
| 6,720,459 B2 | 4/2004 | Sunkara et al. |
| 7,038,092 B2 | 5/2006 | Sunkara et al. |
| 2002/0007043 A1* | 1/2002 | Sunkara et al. ............... 528/396 |
| 2004/0225161 A1 | 11/2004 | Sunkara et al. |
| 2004/0225162 A1 | 11/2004 | Sunkara et al. |
| 2004/0260125 A1 | 12/2004 | Seapan et al. |
| 2005/0069997 A1 | 3/2005 | Adkesson et al. |
| 2008/0004392 A1 | 1/2008 | Qiu et al. |

FOREIGN PATENT DOCUMENTS

| | | |
|---|---|---|
| WO | 0111070 A2 | 2/2001 |
| WO | 2009059140 A2 | 5/2009 |
| WO | 2009059148 A2 | 5/2009 |

OTHER PUBLICATIONS

W. Baker et al., Cyclic Esters of Sulfuric Acid, II. Constitution of Methylene and Glyoxal Sulfates and the Reaction of Methylene Sulfate With Tertiary Bases, J. American Chemical Society (1932), pp. 86-91. Abstract Attached (Journal Article Not Available).
J. Lichtenberger et al., Diol Sulfates, Bulletin De La Societe Chimique De France (1948), pp. 1002-1012. Abstract Attached (Journal Article Not Available).
N. Bouloc et al., Polyethers: A Solid-Phase Iterative Approach, J. Comb. Chem., vol. 3 (2001), pp. 6-8.
Y-P Hsieh, Division S-3 Soil Microbiology & Biochemistry, Pool Size and Mean Age of Stable Soil Organic Carbon in Cropland, Soil Sci. Soc. Am. J., vol. 56 (1992) pp. 460-464.
E. T. Kaiser et al., The Hydrolysis of Some Cyclic Esters of Sulfuric Acid, JACS, vol. 85 (1963), pp. 602-607.
O. Muraoka et al., Synthesis and Biological Evaluation of Deoxy Salacinols, The Role of Polar Substituents in the Side Chain on the α-Glucosidase Inhibiroty Activity, Bioorganic & Medicinal Chemistry, vol. 14 (2006), pp. 500-509.
V. Samano et al., Synthesis of Ultra-Short-Acting Neuromuscular Blocker GW 0430: A Remarkably Stereo- and Regioselective Synthesis of Mixed Tetrahydroisoquinolinium Chlorofumarates, Organic Letters vol. 1, No. 12 (1999), pp. 1993-1996.
V. Samano et al., Supporting Information—Synthesis of Ultra-Short-Acting Neuromuscular Blocker GW 0430: A Remarkably Stereo- and Regioselective Synthesis of Mixed Tetrahydroisoquinolinium Chlorofumarates, Organic Letters vol. 1, No. 12 (1999), pp. 1-11.
D. Weber et al., 13C-Pattern of Natural Glycerol: Origin and Practical Importance, J. Agric. Food Chem. vol. 45 (1997), pp. 2042-2046.

* cited by examiner

*Primary Examiner* — Randy Gulakowski
*Assistant Examiner* — Shane Fang

(57) ABSTRACT

Polyalkylene ether glycol or copolymer thereof are prepared by contacting at least one alkanediol with a alkanediol containing cyclic sulfate.

13 Claims, No Drawings

PROCESS FOR THE PREPARATION OF POLYALKYLENE ETHER GLYCOL

FIELD OF THE INVENTION

This invention relates to a process for preparing polytrimethylene ether glycols or copolymers thereof.

BACKGROUND

Polytrimethylene ether glycols can be produced via the acid-catalyzed polycondensation of 1,3-propanediol, optionally in the presence of comonomer diols. Standard methods of producing polytrimethylene ether glycols using acid catalysis are described in U.S. Pat. No. 6,720,459, U.S. Pat. No. 3,326,985, and U.S. Pat. No. 2,520,733.

One standard catalyst is sulfuric acid. However, there are many safety considerations when using sulfuric acid. There is a need for a replacement catalyst that functions as well as or better than sulfuric acid but has none of the safety and environmental drawbacks of sulfuric acid

SUMMARY

One aspect of the invention is a process comprising:
(a) contacting at least one alkanediol and a composition of Formula (I):

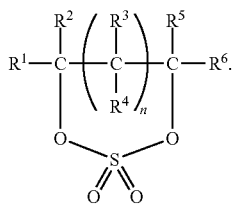

wherein $R^1$, $R^2$, $R^3$, $R^4$, $R^5$ and $R^6$ are independently hydrogen or an $C_1$ through $C_6$ alkyl group, and n is 0-2; to form a polyalkylene ether glycol or copolymer thereof.

DETAILED DESCRIPTION

Described herein is a process comprising:
(a) contacting at least one alkanediol and a composition of Formula (I):

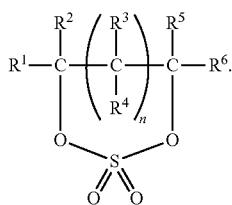

wherein $R^1$, $R^2$, $R^3$, $R^4$, $R^5$ and $R^6$ are independently hydrogen or an $C_1$ through $C_6$ alkyl group, and n is 0-2; to form a polyalkylene ether glycol or copolymer thereof.

The compounds of Formula (I) have the advantage of being solid at room temperatures and easily recrystallized in high purity, aiding in catalyst purification. For example, where n is 1 and $R^1$, $R^2$, $R^3$, $R^4$, $R^5$, and $R^6$ are hydrogen, the melting point is 58-62° C. at ambient pressure. Additional benefits to may be found with ease in handling, transport, and storage, as compared to acid catalysts typically used in similar processes.

By "alkyl" it is meant a straight chain, branched or cyclic arrangement of carbon atoms connected by single carbon to carbon bonds and/or by ether linkages, and substituted accordingly with hydrogen atoms. Common examples of such alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl. In one embodiment, $R^1$, $R^2$, $R^3$, $R^4$, $R^5$ and $R^6$ are $C_1$ through $C_2$ alkyl groups or hydrogen. In another embodiment, $R^1$, $R^2$, $R^3$, $R^4$, and $R^5$ are hydrogen $R^6$ is methyl. In yet another embodiment, $R^1$, $R^2$, $R^3$, $R^4$, $R^5$ and $R^6$ are the same, typically hydrogen. In one embodiment n is 0-1, typically 1.

The alkanediol typically comprises (1) at least one alkanediol selected from 1,3-propanediol or oligomers of 1,3-propanediol having a degree of polymerization of 2-6; and (2) optionally, at least one comonomer diol selected from the group consisting of ethanediol, $C_4$ through $C_{12}$ straight-chain diols, and $C_3$ through $C_{12}$ branched diols. In one embodiment, the alkanediol is 1,3-propanediol, a dimer of 1,3-propanediol or a trimer of 1,3-propanediol. The alkanediol can also be a mixture of one or more alkanediols.

The 1,3-propanediol may be obtained by any of the various well known chemical routes or by biochemical transformation routes. Preferred routes are described in, for example, U.S. Pat. No. 5,015,789, U.S. Pat. No. 5,276,201, U.S. Pat. No. 5,284,979, U.S. Pat. No. 5,334,778, U.S. Pat. No. 5,364,984, U.S. Pat. No. 5,364,987, U.S. Pat. No. 5,633,362, U.S. Pat. No. 5,686,276, U.S. Pat. No. 5,821,092, U.S. Pat. No. 5,962,745, U.S. Pat. No. 6,140,543, U.S. Pat. No. 6,232,511, U.S. Pat. No. 6,235,948, U.S. Pat. No. 6,277,289, U.S. Pat. No. 6,297,408, U.S. Pat. No. 6,331,264, U.S. Pat. No. 6,342,646, U.S. Pat. No. 7,038,092, US20040225161A1, US20040260125A1, US20040225162A1 and US20050069997A1.

Preferably, the 1,3-propanediol is obtained biochemically from a renewable source ("biologically-derived" 1,3-propanediol).

A particularly preferred source of 1,3-propanediol is via a fermentation process using a renewable biological source. As an illustrative example of a starting material from a renewable source, biochemical routes to 1,3-propanediol (PDO) have been described that utilize feedstocks produced from biological and renewable resources such as corn feed stock. For example, bacterial strains able to convert glycerol into 1,3-propanediol are found in the species *Klebsiella*, *Citrobacter*, *Clostridium*, and *Lactobacillus*. The technique is disclosed in several publications, including U.S. Pat. No. 5,633,362, U.S. Pat. No. 5,686,276 and U.S. Pat. No. 5,821,092. U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

The biologically-derived 1,3-propanediol, and polymers based thereon, may be distinguished from similar compounds produced from a petrochemical source or from fossil fuel carbon by dual carbon-isotopic finger printing. This method usefully distinguishes chemically-identical materials, and apportions carbon in the copolymer by source (and possibly year) of growth of the biospheric (plant) component. The isotopes, 14C and 13C, bring complementary information to this problem. The radiocarbon dating isotope (14C), with its nuclear half life of 5730 years, clearly allows one to apportion specimen carbon between fossil ("dead") and biospheric ("alive") feedstocks (Currie, L. A. "Source Apportionment of Atmospheric Particles," Characterization of Environmental Particles, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of 14C concentration in the atmosphere leads to the constancy of 14C in living organisms. When dealing with an isolated sample, the age of a sample can be deduced approximately by the relationship:

$$t=(-5730/0.693)\ln(A/A_0)$$

wherein t=age, 5730 years is the half-life of radiocarbon, and A and $A_0$ are the specific $^{14}C$ activity of the sample and of the modern standard, respectively (Hsieh, Y., *Soil Sci. Soc. Am J.*, 56, 460, (1992)). However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of ca. $1.2\times10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_m \approx 1.1$.

The stable carbon isotope ratio (13C/12C) provides a complementary route to source discrimination and apportionment. The 13C/12C ratio in a given biosourced material is a consequence of the 13C/12C ratio in atmospheric carbon dioxide at the time the carbon dioxide is fixed and also reflects the precise metabolic pathway. Regional variations also occur. Petroleum, C3 plants (the broadleaf), C4 plants (the grasses), and marine carbonates all show significant differences in 13C/12C and the corresponding δ 13C values. Furthermore, lipid matter of C3 and C4 plants analyze differently than materials derived from the carbohydrate components of the same plants as a consequence of the metabolic pathway. Within the precision of measurement, 13C shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric CO2. Two large classes of vegetation are those that incorporate the "C3" (or Calvin-Benson) photosynthetic cycle and those that incorporate the "C4" (or Hatch-Slack) photosynthetic cycle.

C3 plants, such as hardwoods and conifers, are dominant in the temperate climate zones. In C3 plants, the primary CO2 fixation or carboxylation reaction involves the enzyme ribulose-1,5-diphosphate carboxylase and the first stable product is a 3-carbon compound. C4 plants, on the other hand, include such plants as tropical grasses, corn and sugar cane. In C4 plants, an additional carboxylation reaction involving another enzyme, phosphenol-pyruvate carboxylase, is the primary carboxylation reaction. The first stable carbon compound is a 4-carbon acid, which is subsequently decarboxylated. The CO2 thus released is refixed by the C3 cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) (Weber et al., *J. Agric. Food Chem.*, 45, 2942 (1997)). Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$" values are in parts per thousand (per mil), abbreviated ‰, and are calculated as follows:

$$\delta^{13}C \equiv \frac{(^{13}C/^{12}C)\text{sample} - (^{13}C/^{12}C)\text{standard}}{(^{13}C/^{12}C)\text{standard}} \times 1000\text{‰}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Preferably the 1,3-propanediol used as the alkanediol or as a component of the alkanediol will have a purity of greater than about 99%, and more preferably greater than about 99.9%, by weight as determined by gas chromatographic analysis. Particularly preferred are the purified 1,3-propanediols as disclosed in U.S. Pat. No. 7,038,092, US20040260125A1, US20040225161A1 and US20050069997A1.

The at least one comonomer diol can be selected from the group consisting of 1,2-ethanediol, 2-methyl-1,3-propanediol, 2,2'-dimethyl-1,3-propanediol, 1-6-hexanediol, 1,7-heptanediol, 1,7-octanediol, 1,10-decanediol, and 1,12-dodecanedio, typically 1,2-ethanediol. The comonomer diol can comprise up to about 50% by weight in the process mixture.

In one embodiment, the process can be carried out using at least one alkanediol reactant selected from the group consisting of 1,3-propanediol, a dimer of 1,3-propanediol, a trimer of 1,3-propanediol, and mixtures thereof, and at least one comonomer diol selected from the group consisting of ethanediol, $C_4$ through $C_{12}$ straight-chain diols, and $C_3$ through $C_{12}$ branched diols. In a more specific embodiment, the process can be carried out using at least one alkanediol reactant selected from the group consisting of 1,3-propanediol, a dimer of 1,3-propanediol, a trimer of 1,3-propanediol, and mixtures thereof, and at least one comonomer diol selected from the group consisting of 1,2-ethanediol, 2-methyl-1,3-propanediol, 2,2'-dimethyl-1,3-propanediol, 1-6-hexanediol, 1,7-heptanediol, 1,7-octanediol, 1,10-decanediol, and 1,12-dodecanediol. In an even more specific aspect, the process can be carried out using at least one alkanediol reactant selected from the group consisting of 1,3-propanediol, a dimer of 1,3-propanediol, a trimer of 1,3-propanediol, and mixtures thereof, and 1,2-ethanediol. In an even more specific embodiment, the at least one alkanediol reactant is 1,3-propanediol and the at least one comonomer diol is 1,2-ethanediol.

Thermal stabilizers, antioxidants, such as butylated hydroxyl toluene, and coloring materials may also be added to the reaction mixture or to the final polymer if necessary.

The process may be carried out under an inert atmosphere, such as nitrogen or argon. In another aspect, the reaction is carried out at a pressure of less than one atmosphere; in additional aspects the process is carried out at a pressure of less than 50 kPa or less than 25 kPa.

The reaction is typically carried out in the presence of water. Water is produced during the reaction but if additional water is desired, it may be introduced either before the reaction is started, in one or more aliquots, or continuously throughout the duration. The concentration of water during the reaction is typically about 0.01 weight % to about 10 weight %.

The composition of Formula (I) is present at a concentration of typically 0.01 to about 10.0 mole %, or more typically about 0.02 to about 5.0 mole %, relative to the alkanediol.

In one embodiment, the process is carried out at a temperature of about 120° C. to about 250° C. In another embodiment, the process is carried out at a temperature of about 120° C. to about 210° C., or about 140° C. to about 190° C.

The time for the process will depend on many factors, such as the reactants, reaction conditions and reactor. One skilled in the art will know to adjust the time for the reaction to achieve high yields of a reaction product having a desired molecular weight.

In one aspect, the molecular weight (Mn) of the polyalkylene ether glycol product is at least about 2000 g/mole, typically at least about 1000 g/mole or least about 250 g/mole.

The process is not limited by reactor configuration, however a successful manufacturing process for polytrimethylene ether glycol should provide the product within a desired time and under conditions to achieve the average molecular weight for end use applications and to limit the production of undesired chemical species that would make the product unsuitable for end use applications or that would require costly measures to remove, for example product having high degree of unsaturation or high color. Reactor configurations, as well as a continuous process for polycondensation of 1,3-propanediol reactant, are described in U.S. Pat. No. 6,720,459, Column 5, line 49 through Column 9, line 26, and FIGS. 1 through 6. The present process can be carried out in a closed system with no fresh monomer being added over the course of the reaction. The process can also be carried out with fresh monomer being added to the process mixture and/or product being withdrawn from the reaction mixture over the course of the reaction. The latter can be used to achieve a continuous reaction process. In addition, a "high-to-low" temperature profile can be carried out within one reactor or reactor zone, or in multiple reactors or zones of a reactor. For example, the process can be initiated in one reactor or reactor zone, and as the temperature is modified (for example, decreased) to achieve a "high-to-low" profile, the reaction mixture can be transferred to a different reactor or reactor zone. The number of reactors, or reaction zones within a reactor, will be determined in part by the cost of the reactor(s) and the temperature profile of the reaction.

The at least one polytrimethylene glycol or copolymer thereof in the reaction product produced as described in any of the aspects of the invention can be recovered by methods known in the art, such as extraction.

The polytrimethylene glycol or copolymer thereof are useful, for example, in the formation of thermoplastic elastomers, as lubricants, and as fibers for textiles.

EXAMPLES

Materials and Methods

Characterization of Polytrimethylene Ether Glycol by $^1$H NMR Spectroscopy

A comparison of relative integral values by $^1$H NMR was used for the characterization of both crude and purified polymers. Derivatization of reactive end groups with trifluoroacetic anhydride (TFAA) was used. In a typical preparation, 30 mg of polymer was dissolved in 650 microliter $CDCl_3$ followed by careful addition of 200 microliter TFAA.

The $^1$H NMR spectra was used to determine the relative amount of unreacted OH ends, ethers, and unsaturated end groups:

F3COCO—(CH2CH2CH2O)$_n$—COCF3 (t, 4H, 4.40-4.47 ppm)

F3COCO—(CH2CH2CH2O)$_n$—COCF3 (m, 4H, 3.45-3.65 ppm)

H2CCHCH2(OCH2CH2CH2)$_n$—OCOCF3 (dd, 2H, 5.15-5.29 ppm)

H2CCHCH2(OCH2CH2CH2)$_n$—OCOCF3 (m, 1H, 5.83-5.94 ppm)

These relative integral values were used for the subsequent determination of degree of polymerization (DP), molecular weight average (Mn), and unsaturated end groups as shown below:

The degree of polymerization (DP) was determined by the following:

$$DP = (\text{area of } I + \text{area of } II + 2 \cdot \text{area } IIIb)/(\text{area of } I + 2 \cdot \text{area } IIIb)$$

The molecular weight average (Mn) was determined by the following:

$$Mn = DP \cdot 58.08 + 18.02$$

The total end groups (meq/kg) were determined by the following:

$$\text{Total end groups(meq/kg)} = 2 \cdot 1 \times 10^6 / Mn$$

The total unsaturated end groups (meq/kg) were determined by the following:

$$\text{Unsaturated end groups(meq/kg)} = \text{total ends} \cdot (2 \cdot \text{area of } IIIb)/(2 \cdot \text{area of } IIIb + \text{area of } I)$$

Polymer color was measured according to ASTM standard D-1209 as APHA values (Platinum-Cobalt system) using standard spectrophotometer/colorimeter instruments such as type "SMART 2", LaMotte, Chestertown, Md., USA, type "Color Quest XE", Hunterlab, Reston, Va., USA, and type "Cary 50 Conc", Varian Inc., Palo Alto, Calif., USA.

1,3-Propanediol Cyclic Sulfate

All examples utilized 1,3-propanediol cyclic sulfate purchased from Sigma-Aldrich (St. Louis, Mo.) and used as received unless otherwise specified.

1,3-propanediol cyclic sulfate was prepared using a procedure modified from Guijarro, D. et. al. Tetrahedron 1994, 50(11), 3427-3436; Samano, V. et. al. Org. Lett. 1999, 12 (1), 1993-1996; and Muraoka, O. et. al. Bioorganic & Medicinal Chemistry 2006, 14, 500-509. Renewably sourced 1,3-propanediol (E. I. du Pont de Nemours and Company, Wilmington, Del.) (15.0 g, 197.13 mmol, 1 eq.) was dissolved in $CHCl_3$ (100 ml) and charged into a 250 round bottomed flask equipped with magnetic stir bar. The system was cooled with ice/water bath to which thionyl chloride (28.14 g, 236.56 mmol, 1.2 eq.) was added. The system was allowed to warm to ambient temperature at which point it was then heated to reflux for 1.5 hours.

The solution was then re-cooled to 0° C. and diluted with 100 ml of acetonitrile. To this was added sequentially $RuCl_3 \cdot H_2O$ (0.025 g, 0.12 mmol, 0.006 eq.), $NaIO_4$ (62.98 g, 295.70 mmol, 1.5 eq), and 375 ml of $H_2O$. The mixture was allowed to warm to ambient temperature and continued to stir for 1.5 hours.

The solution was then diluted and extracted with diethyl ether. The organics were combined and washed with $NaHCO_3$, brine, and water. The organic layer was dried with $MgSO_4$, filtered through a bed of silica to remove baseline byproducts, and concentrated in vacuo. Recrystallization from ethyl acetate/hexanes provided the final product as white crystals. The physical and spectral properties of 1,3-propanediol cyclic sulfate were measured using standard techniques:

IR $(cm^{-1})$: 1196, 1391; $^1$H NMR (400 MHz): δ 2.13 (m, 2H), 4.71 (t, 4H, J=5.1, 10.9); $^{13}$C NMR (100 MHz) δ 23.56; 73.08; C, H, S calcd for $[C_3H_6C_4S]$: C, 26.08; H, 4.38; S, 23.21. found C, 26.32; H, 4.39; S, 23.13.

Example 1

Biologically-derived 1,3-propanediol (E. I. du Pont de Nemours and Company, Wilmington, Del.) (50.00 g, 657.95 mmol, 1.0 eq.) was charged into a 3-neck 100 cc flask. To this 3.0 wt % 1,3-propanediol cyclic sulfate (1.50 g, 10.86 mmol, 0.017 eq.) was added. The flask was connected to a condenser and collection flask which was placed on ice. The vessel was placed under a flow of nitrogen at 200 sccm and the reaction was slowly heated to 120° C. at which point water was added via syringe pump at 1 ml/h for the duration of the run. After 1 h, the temperature was increased to 170° C. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 78 | 0 | — |
| 2.0 | 101 | 0 | — |
| 3.0 | 447 | 13 | — |
| 4.0 | 936 | 12 | — |
| 4.5 | 1310 | 20 | 43 |
| 5.0 | 2014 | 21 | — |
| 6.0 | 2552 | 24 | — |
| 7.0 | 3243 | 29 | — |
| 8.0 | 3412 | 45 | 495 |

Example 2

Biologically-derived 1,3-propanediol (E. I. du Pont de Nemours and Company, Wilmington, Del.) (50.00 g, 657.11 mmol, 1.0 eq.) was charged into a 3-neck 100 cc flask. To this 2.11 wt % 1,3-propanediol cyclic sulfate (1.05 g, 7.60 mmol, 0.012 eq.) was added. The flask was connected to a condenser and collection flask which was placed on ice. The vessel was placed under a flow of nitrogen at 200 sccm and the reaction was slowly heated to 120° C. at which point water was added via syringe pump at 1 ml/h for the duration of the run. After 1 h, the temperature was increased to 170° C. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 177 | 4 | — |
| 2.0 | 408 | 9 | — |
| 3.0 | 680 | 11 | — |
| 4.0 | 1147 | 16 | — |
| 5.0 | 1781 | 14 | 35 |
| 6.0 | 2406 | 17 | 152 |

Example 3

Biologically-derived 1,3-propanediol (E. I. du Pont de Nemours and Company, Wilmington, Del.) (50.00 g, 657.11 mmol, 1.0 eq.) was charged into a 3-neck 100 cc flask. To this 2.11 wt % 1,3-propanediol cyclic sulfate (1.05 g, 7.60 mmol, 0.012 eq.) was added. The flask was connected to a condenser and collection flask which was placed on ice. The vessel was placed under a flow of nitrogen at 200 sccm and the stir rate was set to approximately 600 rpm. The reaction was slowly heated to 170° C. at which point water was added via syringe pump at 1 ml/h for the duration of the run. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 0.5 | 130 | 5 | — |
| 1.0 | 252 | 9 | — |
| 2.0 | 783 | 17 | — |
| 3.0 | 1759 | 30 | 190 |
| 4.0 | 2826 | 50 | — |
| 5.0 | 3421 | 84 | — |
| 6.0 | 3650 | 99 | 702 |

Example 4

Biologically-derived 1,3-propanediol (E. I. du Pont de Nemours and Company, Wilmington, Del.) (50.00 g, 657.11 mmol, 1.0 eq.) was charged into a 3-neck 100 cc flask. To this 2.11 wt % 1,3-propanediol cyclic sulfate (1.05 g, 7.60 mmol, 0.012 eq.) was added. The flask was connected to a condenser and collection flask which was placed on ice. The vessel was placed under a flow of nitrogen at 200 sccm and the stir rate was set to approximately 950 rpm. The reaction was slowly heated to 170° C. at which point water was added via syringe pump at 1 ml/h. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 228 | 8 | — |
| 2.0 | 602 | 13 | — |
| 3.0 | 971 | 15 | — |
| 3.5 | 1132 | 16 | — |
| 4.0 | 1378 | 15 | 44 |
| 5.0 | 1727 | 15 | — |
| 6.0 | 2145 | 14 | 67 |

Example 5

Biologically-derived 1,3-propanediol (E. I. du Pont de Nemours and Company, Wilmington, Del.) (50.00 g, 657.11 mmol, 1.0 eq.) was charged into a 3-neck 100 cc flask. To this 2.11 wt % 1,3-propanediol cyclic sulfate recrystallized from ethyl acetate/hexane (1.05 g, 7.60 mmol, 0.012 eq.) was added. The flask was connected to a condenser and collection flask which was placed on ice. The vessel was placed under a flow of nitrogen at 200 sccm and the stir rate was set to approximately 950 rpm. The reaction was slowly heated to 170° C. at which point water was added via syringe pump at 1 ml/h. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 208 | 7 | — |
| 2.0 | 442 | 12 | — |
| 3.0 | 772 | 14 | — |
| 4.0 | 1203 | 17 | — |
| 4.5 | 1562 | 18 | 41 |
| 5.0 | 1932 | 19 | 64 |
| 6.0 | 2208 | 21 | 76 |

Example 6

Biologically-derived 1,3-propanediol (E. I. du Pont de Nemours and Company, Wilmington, Del.) (800.4 g, 10.52 mol, 1.0 eq.) was charged into a 1000 cc Morton reactor equipped with a condenser and an agitator. To this 2.01 wt % 1,3-propanediol cyclic sulfate recrystallized from ethyl acetate/hexane (16.1 g, 116.55 mmol, 0.012 eq.) was added and purged with $N_2$ at a rate of 0.5 L/min. Water was introduced via syringe pump at 18 ml/h. The reactor flask was connected to a condenser and collection flask. The time at which the heating started was set as reaction starting point. The reactant mixture reached temperature within 1.25 hours and polymerization was allowed to proceed at 183° C. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 352 | 13 | 34 |
| 2.0 | 668 | 18 | 39 |
| 3.0 | 948 | 17 | 43 |
| 4.0 | 1163 | 17 | 51 |
| 5.0 | 1314 | 16 | 54 |
| 6.0 | 1410 | 18 | 52 |

Example 7

Biologically-derived 1,3-propanediol (E. I. du Pont de Nemours and Company, Wilmington, Del.) (800.4 g, 10.52 mol, 1.0 eq.) was charged into a 1000 cc Morton reactor equipped with a condenser and an agitator. To this 2.01 wt % 1,3-propanediol cyclic sulfate prepared from biologically-derived 1,3-propanediol (16.1 g, 116.55 mmol, 0.012 eq.) was added and purged with $N_2$ at a rate of 0.5 L/min. Water was introduced via syringe pump at 18 ml/h. The reactor flask was connected to a condenser and collection flask. The time at which the heating started was set as reaction starting point. The reactant mixture reached temperature within 1.25 hours and polymerization was allowed to proceed at 183° C. Samples were taken periodically from the reaction flask for color measurement, molecular weight and unsaturated end groups analysis as described above. The results are shown below.

| Time Point (h) | Mn (g/mol) | Unsaturation (meq/kg) | Color (APHA-YI) |
|---|---|---|---|
| 1.0 | 377 | 17 | 59 |
| 2.0 | 703 | 18 | 61 |
| 3.0 | 977 | 22 | 70 |
| 4.0 | 1160 | 20 | 77 |
| 5.0 | 1301 | 19 | 82 |
| 6.0 | 1403 | 22 | 87 |

What is claimed is:

1. A process comprising:
   (a) contacting at least one alkanediol and a composition of Formula (I):

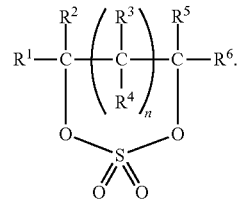

wherein $R^1$, $R^2$, $R^3$, $R^4$, $R^5$ and $R^6$ are independently hydrogen or an $C_1$ through $C_6$ alkyl group, and n is 0-2;
   to form a polyalkylene ether glycol or copolymer thereof, wherein the composition of Formula (I) is added to a reaction mixture comprising the at least one alkanediol.

2. The process of claim 1 wherein the alkanediol comprises (1) at least one alkanediol selected from 1,3-propanediol or oligomers of 1,3-propanediol having a degree of polymerization of 2-6; and (2) optionally, at least one comonomer diol selected from the group consisting of ethanediol, $C_4$ through $C_{12}$ straight-chain diols, and $C_3$ through $C_{12}$ branched diols.

3. The process of claim 2, where the alkanediol is 1,3-propanediol, a dimer of 1,3-propanediol or a trimer of 1,3-propanediol, or mixtures thereof.

4. The process of claim 2, wherein the comonomer diol is 1,2-ethanediol, 2-methyl-1,3-propanediol, 2,2'-dimethyl-1,3-propanediol, 1-6-hexanediol, 1,7-heptanediol, 1,7-octanediol, 1,10-decanediol, or 1,12-dodecanediol.

5. The process of claim 1 wherein $R^1$, $R^2$, $R^3$, $R^4$, $R^5$ and $R^6$ are hydrogen and n is 1.

6. The process of claim 1 wherein $R^1$, $R^2$, $R^3$, $R^4$, $R^5$ and $R^6$ are hydrogen and n is 0.

7. The process of claim 1 wherein $R^1$, $R^2$, $R^3$, $R^4$, and $R^5$ are hydrogen, $R^6$ is methyl, and n is 0.

8. The process of claim 1 wherein the polyalkylene ether glycol or copolymer thereof has a number-average molecular weight of at least about 250 g/mole.

9. The process of claim 1 wherein the polyalkylene ether glycol or copolymer thereof has a number-average molecular weight of at least about 1000 g/mole.

10. The process of claim 1, wherein the composition of Formula (I) is present at a concentration of about 0.01 to about 10.0 mole % relative to the alkanediol.

11. The process of claim 1, wherein the composition of Formula (I) is present at a concentration of about 0.02 to about 5.0 mole % relative to the alkanediol.

12. The process of claim 1, wherein the contacting is performed at a temperature from about 120° C. to about 250° C.

13. The process of claim 1, wherein the process is carried out under an inert atmosphere.

* * * * *